United States Patent [19]

Helioff et al.

[11] Patent Number: 4,793,994

[45] Date of Patent: Dec. 27, 1988

[54] COMPOSITIONS USED IN PERMANENT STRUCTURE ALTERING OF HAIR

[75] Inventors: Michael W. Helioff, Westfield; Carmen D. Bires, Long Valley; Robert B. Login, Oakland, all of N.J.

[73] Assignee: GAF Corporation, Wayne, N.J.

[21] Appl. No.: 13,617

[22] Filed: Feb. 12, 1987

Related U.S. Application Data

[63] Continuation-in-part of Ser. No. 879,776, Jun. 27, 1986, abandoned.

[51] Int. Cl.4 ............................................. A61K 7/09
[52] U.S. Cl. ....................................... 424/71; 424/72
[58] Field of Search ............................ 424/70, 71, 72

[56] References Cited

U.S. PATENT DOCUMENTS

| | | | |
|---|---|---|---|
| 3,988,318 | 10/1976 | Copes et al. | 260/239.3 |
| 3,988,350 | 10/1976 | Copes et al. | 260/326.5 |
| 4,557,934 | 12/1985 | Cooper | 424/128 |

OTHER PUBLICATIONS

Zienty and Steahly, "N-Substituted 2-Pyrrolidones", J. of the Amer. Chem. Soc., vol. 80, Mar. 1947, pp. 715–717.

Primary Examiner—Joseph L. Schofer
Assistant Examiner—Jeffrey T. Smith
Attorney, Agent, or Firm—Marilyn J. Maue; Joshua J. Ward

[57] ABSTRACT

A composition comprising an aqueous preparation on the basis of keratin softening, which contains as a swelling and penetration agent, an N-alkyl pyrrolidone wherein the alkyl group contains between 8 and 22 carbon atoms.

24 Claims, No Drawings

COMPOSITIONS USED IN PERMANENT STRUCTURE ALTERING OF HAIR

This application is a continuation-in-part of U.S. patent application Ser. No. 879,776 filed June 27, 1987, now abandoned.

In one aspect the invention relates to an aqueous composition containing a softening and penetrating agent for keratin protein reduction which agent enhances cleavage of the disulfide bond of the hair cystine residue to form the corresponding cysteine residue in a process for altering the structure and/or configuration of hair as in straightening or permanent waving. In another aspect, the invention relates to an agent which promotes hard water solubility of a neutralizing lotion employed in a reducing process for altering the structure and/or configuration of hair.

BACKGROUND OF THE INVENTION

The activity or effectiveness of hair shaping preparations is based mainly on the inclusion therein of an agent for softening and relaxing the keratin protein present in hair by reducing the disulfide linkages of keratin. The hair fiber is wound on rods to achieve the desired waving effect or manipulated into a straightened condition and allowed to remain wetted with the reducing lotion for a desired period, after which the reducing lotion is rinsed off and finally oxidized with a neutralizing solution or air oxidized.

Basically, hair is softened and swelled by rupture of disulfide bonds present in the cystine component of keratin by the use of a mild alkaline reducing agent. Cleavage of at least some of the disulfide bonding to form the corresponding cysteine residue is necessary to allow for molecular rearrangement which takes place during the hair fiber molding operation. The reductive fission of hair disulfides generally causes reddening of the scalp area and damage to the hair fiber, particularly hair which has been bleached, tinted or otherwise damaged. Current hair structure altering lotions which provide relaxation of imposed stress include aqueous solutions of alkaline mercapto compounds, sulfites or bisulfites at a pH of between 7 and 9.5. In order to obtain a permanent effect, particularly in hair straightening, it is often necessary to introduce the active agent in relatively high concentration with the result that the reducing lotion is provided at almost the limit of its physiological compatability or tolerability.

Damage to hair is increased where heat waving, as opposed to cold waving, is employed. Of the reducing agents currently in use, the thioglycolates or thioglycolic acid, dithioglycolic acid and mercapto compounds such as ammonium thioglycolate, glyceryl, monothioglycolate, mercapto propionic acid and mercapto ethyl amine are most often employed in professional waving or hair straightening. Alkaline sulfites and bisulfites are generally reserved for home permanent use. In addition to the reducing agent, alkalis having a dissociation constant less than $5 \times 10^{-3}$, are also used to facilitate diffusion through the hair. These promoters include ammonia, ammonium hydroxide, ethanol amine, diisopropanol amine, glycine, and lysine.

All of the above reducing lotions cause some degree of hair damage depending on the tightness and thickness of the curl, the temperature of processing, the concentration of the alkaline reducing agent and the condition of the hair. Additionally, many reducing lotions produce a disagreeable odor during reduction of the cystine molecule.

Accordingly, the art has sought means and possibilities whereby to provide for the aforesaid waving and straightening lotions, compositions which are less damaging to the skin and hair and which are simple to incorporate into the standard reducing lotions currently in use so as to provide the same or more effective results for heat or cold permanent waving and hair straightening. Realization of these objects can be achieved by promoting penetration of the reducing lotion and providing absorption at a faster rate so that the time hair fiber is exposed to chemical action is reduced. Secondary aims include masking the thiol odor of the reducing lotion and minimizing skin irritation caused by routine exposure of professional hair dressers or erythema on the scalp and neck of the subject undergoing treatment.

Accordingly, it is an object of this invention to achieve the various aims enumerated above by a single and commercially feasible process involving the addition of the compound of the present invention as a component in standard hair structure and configuration altering lotions used both professionally and at home.

Another object of the invention is to provide an additive to hair reducing lotions which promotes a higher degree of curl in a shorter period of time.

Another object of the invention is to provide an additive which actually conditions the hair undergoing restructuring treatment.

Another object is to provide a compound which, when added to a hair waving or straightening lotion, increases the penetration rate of the lotion to minimize run-off and dripping.

Yet another object is to provide a long lasting hair permanent that moisturizes and protects the hair fiber so as to give the processed hair a silky softness.

Still another object is to provide an additive which improves hard water solubility of components in the neutralizing lotion.

These and other objects of the invention will become apparent from the following description and disclosure.

THE INVENTION

In accordance with the present invention there is provided a N-alkyl lactam which is incorporated into a hair waving or straightening lotion at a concentration of between about 0.01 to about 7 wt. %, preferably between about 0.05 and about 5 wt. % based on total weight of the respective treating lotions. The alkyl lactams of the present invention are defined by the structure

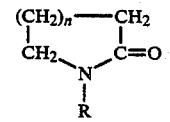

wherein n has a value of from 1 to 3 and R is alkyl having from 8 to 22 carbon atoms. Of these, pyrrolidones wherein R is octadecyl, hexadecyl, octyl, isooctyl, hydrogenated tallow, coco or dodecyl are preferred. Most preferred of these species is N-dodecyl pyrrolidone employed in the reducing lotion at a concentration of between about 0.75 and about 1.50 wt. %.

As the term "lotion" is used herein, it is to be understood that this term includes a cream, a gel, an emulsion or a watery liquid.

The present alkyl lactams can be used individually or in admixtures and can be added to any of the commercial hair waving or straightening lotions including heat or cold permanent waving preparations utilizing water wrap or lotion wrap procedures. Alternatively, structural hair altering preparations may be made up using the components normally included in preparations currently marketed and the N-alkyl lactam added to improve properties. In general, hair waving preparations comprise a reducing lotion and an oxidizing lotion; although some preparations are formulated such that the oxidizing or neutralizing lotion can be omitted. Most home perm and milder waving lotions can simply be washed off the hair fiber by rinsing with water and are therefore categorized as self-neutralizing.

Generally, the hair waving or straightening lotion contains a mild reducing agent which is exemplified by the most commonly used ammonium thioglycolate in a solution having a pH of between about 7 and 10.5, preferably between about 8.5 and about 9.5. Other reducing agents which have found commercial use include glyceryl monothioglycolate employed at a pH of less than 7, thioglycolic acid, dithioglycolic acid, mercaptoethyl amine, mercaptopropionic acid, dithioglycolate and alkali sulfites or bisulfites. The sulfite and bisulfite reducing agents are more commonly employed for home permanents and produce a milder, softer wave. The rate of reaction of these reducing agents increases with pH and temperature, although most are applied at between room temperature and 35° C. for a period of from about 3 to about 15 minutes. The concentration of reducing agent in the aqueous reducing lotion can vary between about 2 and about 20%. Within this range, lower concentrations are employed for damaged or bleached hair whereas for virgin, undamaged hair a concentration in the upper portion of the range can be applied. In the present invention the mole ratio of reducing agent to N-alkyl lactam is between about 3:1 and about 30:1, preferably between about 8:1 and about 20:1.

The reducing lotion is generally employed with an alkali having a dissociation constant less than $5 \times 10^{-3}$. Suitable compounds for alkalization include ammonia, ammonium hydroxide, sodium hydroxide, ethanol amine, diisopropanol amine, an alkali metal salt of an amino acid, e.g. glycine or lysine and guanidine. Alkali in a concentration of between about 0.5 and about 6% or 0.7-1.3 grams of free ammonia per 100 mililiters of solution is normally used.

The reducing lotion may also include a buffer such as ammonium bicarbonate to maintain a desired pH. Other additives which may be employed include catalysts for self-neutralizing permanent wave lotions, opacifiers to promote creamy appearance and fragrance to mask the odor of ammonia and thiol. Fatty acid polypeptide condensates, oxyethylated fatty alcohols and oxyethylated alkyl phenols have been employed as conditioners and emollients to minimize hair damage. However, these conditioning agents only minimally protect against hair damage and do not provide a sufficient moisture barrier to eliminate dryness and splitting at the distal ends of the hair fiber when processed with the reducing lotion.

The reducing lotions of the present invention are generally employed as 50-98% aqueous solutions of deionized water, preferably between about 75 and about 95% aqueous solutions.

The hair can be prerinsed with water or the reducing solution applied directly on the hair wound rods or in a straightened condition for softening and relaxation of the hair fiber. The softening effect is produced by rupture of the disulfide bonds of the cystine residue in the keratin protein to produce the corresponding cysteine residue which can be represented for example by the following reaction

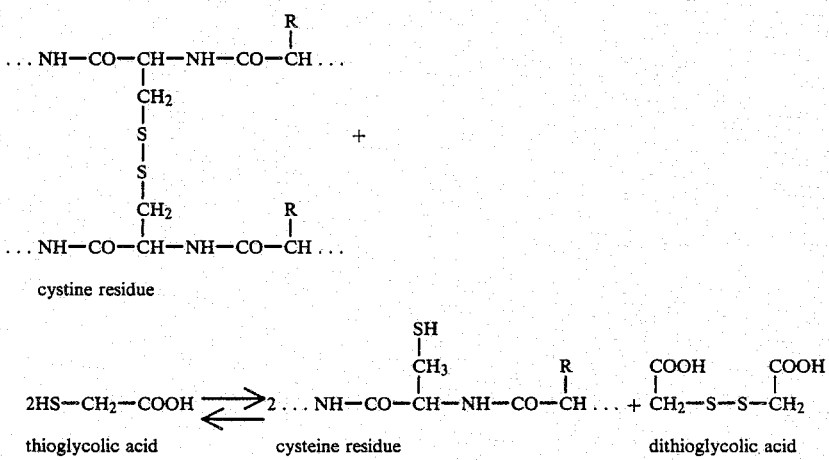

In this relaxed state, the hair fiber, wound on rods or straightened according to the desired structure, is held at room temperature, or slightly increased temperature up to about 50° C. for acceleration of the chemical reaction, for a period of between about 5 and about 20 minutes; after which the reducing solution is water washed from the hair and the disulfide bond are reformed by air oxidation or by the application of an oxidizing lotion which sets the hair according to the desired structure. The degree of curl depends primarily on the size and shape of the rods on which the hair is wound.

Reformation of the cystine residue by oxidation is considerably high, for example up to 90% reformation. Thus, the oxidizing solution which neutralizes the reducer can be regarded as a fixing lotion. Suitable oxidizing agents include hydrogen peroxide, potassium bromate, sodium bromate, sodium perborate, potassium percarbonate and, for the removal of sulfite or bisulfite reducing agents, 8 to 12% of barium chloride or calcium chloride has been used effectively. Other oxidizing agents are employed in 1 to 20% solution in water; although hydrogen peroxide is usually employed as a 1 to 2% aqueous solution.

Some typical reducing hair waving lotions are illustrated by the following formulations.

| Ingredients | % By Weight |
|---|---|
| Single Step Waving Formulation | |
| Ammonium thioglycolate | 0.20 |
| Potassium sulfite | 0.80 |
| Tartaric acid | 0.03 |
| Ethyl alcohol | 1.00 |
| Monoethanolamine | 0.03 |
| Potassium iodide | 0.60 |
| Water | 97.34 |
| Bisulfite Waving Formulation | |
| Water | 55.55 |
| Ammonium bisulfite | 22.00 |
| Hydroxyethyl cellulose | 2.50 |
| Urea | 10.00 |
| Isopropyl alcohol | 5.00 |
| Disodium phosphate | 1.14 |
| Citric acid | 0.46 |
| Ammonium hydroxide | 1.10 |
| Chelating agent | 0.05 |
| Fragrance | 0.20 |
| Surfactant | 2.00 |
| and | |
| Sodium bisulfite | 6.46 |
| Sodium borate | 4.10 |
| Sodium carbonate | 4.10 |
| Monoethanolamine | 4.92 |
| Diethanolamine | 4.92 |
| Wetting agent | 1.00 |
| Water | q.s. to 100.00 |

The basic technical premise underlying permanent hair straightening is similar to that in waving. Hair is softened, maintained straight under tension for a period of time by means of the high viscosity of the product and repeated combing, and after rinsing, rehardened by application of the neutralizer. Many hair-straightening compositions are merely thickened versions of permanent-waving products. For example, alkaline thioglycolate (6–8%) is formulated into thick oil-water emulsion or cream using generous concentrations of cetyl and stearyl alcohols and high molecular weight polyethylene glycol together with a fatty alcohol sulfate as emulsifier which offers an added advantage of ready rinsability. Mixtures of ammonium bisulfite and urea have also found application in hair-straightening. Processing time may be between about 30 minutes and 2 hours, depending on the initial curliness of the hair. Conventional oxidizing neutralizers e.g. $H_2O_2$, bromates, and perborates are most often used in the final step of the process. The reformation of the cystine cross-linkages in bisulfite-reduced hair is effected by a rinse (pH 8–10).

An important class of permanent straighteners in frequent use is based on alkali as an active ingredient. Sodium or potassium hydroxide or sodium carbonate in combination with guanidine are used at concentrations of 1.5–3% in a heavy cream base. Although the recommended treatment time is only 5–20 minutes for this mixture, the straightening effects, in general, surpass those obtained with either thioglycolates or bisulfites because of the greater aggressiveness of the alkaline relaxers. It has been found that a 15-minute treatment irreversibly decreases the cystine content of hair to about two thirds of its initial value.

The damaging action of strong alkali on hair is not restricted to the disulfide bonds alone. Apart from the potential of the main-chain scission, the very nature of the high pH base leads to a build-up of negative charges in hair which results in increased swelling, the latter being intensified by concurrent breakdown of the disulfide bonds.

Typical formulations for hair straightening preparations include the following Examples A-D

| Ingredients | % By Weight |
|---|---|
| A Petrolatum | 76.75 |
| Polyoxyethylene oleyl ether | 21.00 |
| Lactic acid, 90% | 2.20 |
| Thymolphthalein | 0.05 |
| B Water | 42.25 |
| Sodium hydroxide | 2.20 |
| Sodium lauryl ether sulfate | 6.00 |
| Hydrolyzed animal protein | 1.00 |
| Mineral oil | 21.30 |
| Petrolatum | 8.00 |
| Squalene | 3.00 |
| Lauryl alcohol | 1.25 |
| Lanolin fatty acids | 2.00 |
| Cetyl alcohol | 12.00 |
| Sodium isostearoyl-2-lactylate | 1.00 |
| C Emulsifying wax NF (Polawax) | 7.5 |
| Cetyl alcohol (Crodacol C-95) | 1.0 |
| Petrolatum (Protopet) | 4.0 |
| Carnation mineral oil | 15.0 |
| Steareth 2 (Volpo S-2) | 0.5 |
| DEA-oleth-10 phosphate (Crodafos N10N) | 1.5 |
| Propylene glycol | 2.0 |
| Steareth 10 (Volpo S-10) | 2.5 |
| Deionized water | 53.0 |
| NaOH, 25% | 12.0 |
| Diazolidinyl urea (and) methylparaben (and) propylparaben (and) propylene glycol (Germaben II) | 1.0 |
| D i Carbomer 941 (Carbopol 941) | 2.0 |
| Deionized water | 77.8 |
| Triethanolamine | 1.0 |
| ii Ammonium thioglycolate | 13.2 |
| Ammonia | 3.5 |
| Laureth-23 (Emthox 5964) | 0.5 |
| Quaternium-33 (and) ethyl hexanediol (Lanoquat 1756) | 2.0 |

Solutions (i) and (ii) are combined.

Typical oxidizing and neutralizing formulations for permanent waving or straightening lotions include the following.

| | Wt. % |
|---|---|
| Heat Hair Wave Neutralizing Solution | |
| Hydrogen peroxide | 1.3000 |
| Citric acid | 0.5000 |
| Phosphoric acid, adjusted to pH 2.84 | 0.0064 |
| Water | q.s. to 100.0000 |
| Neutralizer with Citrate Buffer | |
| Hydrogen peroxide, 35% sol. | 5.00 |
| Isostearamidopropylmorpholine lactate | 0.75 |
| Cetearyl alcohol/ceteth 20 | 0.50 |
| Mineral oil | 0.07 |
| Methylparaben | 0.10 |
| Phenacetin | 0.10 |
| Fragrance | 0.05 |
| Citric acid | 4.00 |
| Water | q.s. to 100.00 |
| Sodium citrate | q.s. to pH 1.9 |
| Cold Wave Neutralizer with Keratin Hydrolyzate | |
| Sodium bromate | 5.0 |
| Amphoteric surfactant | 0.5 |
| Cationic cellulosic | 0.5 |
| Perfume | 0.1 |
| Keratin hydrolyzate | 2.0 |

-continued

| | Wt. % |
|---|---|
| Water | q.s. to 100.0 |

The N-alkyl lactam, preferably the N-alkyl pyrrolidone, of the present invention can be applied to either or both the reducing and oxidizing lotions employed for permanent waving or straightening of hair to achieve remarkable benefits in the overall processing. Such benefits include a higher degree of curl and curl retention over an extended period, high lubricity on the hair, significant elimination of erythema, masking of thiol odor, hair conditioning action during processing, faster and higher penetration of reducing lotion into the hair and lotion viscosity increase. Incorporation of the present lactams results in hair waving excellent wet and dry combability, improved body and hair of a smooth, soft, lustrous and silky texture after processing. It is theorized that the N-alkyl lactam, particularly the N-alkyl pyrrolidone, penetrates deeply to the cortex of the hair fiber and protects the shaft against damage from within. The present N-alkyl lactams appear to provide a moisture barrier around the hair shaft and gives high substantivity to the hair without interfering with the relaxing process. Further, the present lactams can tolerate usage over a very wide pH range without precipitating out of solution. These and many other advantages are realized by the use of the present compounds.

Having generally described the present invention, reference is now had to the following examples which illustrate preferred embodiments but which are not to be construed as limiting to the scope of the invention as more broadly set forth above and in the appended claims.

EXAMPLE 1

Zotos* permanent waving preparation was used as the standard professional hair waving preparation of this test. This professional product contained a waving lotion and a neutralizing lotion represented as follows.
*Zotos International Inc., Darien, Conn.

| | % by Weight |
|---|---|
| REDUCING LOTION | |
| Ammonium thioglycolate (60 wt. %) | 15.20 |
| Ammonium hydroxide (28 wt. %) | 0.80 |
| Ammonium Bicarbonate buffer | 0.80 |
| Styrene/PVP Copolymer latex Opacifier | 1.60 |
| Igepal CA 630 Surfactant** | 0.20 |
| Deionized water | 80.00 |
| Fragrance | 0.40 |
| NEUTRALIZING LOTION | |
| Hydrogen peroxide | 4.50 |
| Citric acid | 0.20 |
| Polyoxyethylene lauryl ether | 0.50 |
| Latex opacifier | 0.10 |
| Phenacetin | 0.04 |
| Deionized water | 94.26 |
| Fragrance | 0.40 |

*Zotos International Inc., Darien, Connecticut
**1% Aqueous solution of $C_8H_4-C_6H_4-O-(CH_2CH_2O)_{av.9}CH_2CH_2OH$ The hair of test subject was dry, tinted and had been previously permed. In the present treatment, the hair of test subject was saturated with water, allowed to drip dry, after which the hair was sectioned into about 25 sections and the distal ends of each section is wrapped in a porous end paper and rolled on a permanent hair setting rod.

To a one half portion of the above reducing lotion, 1.00% by weight of N-dodecylpyrrolidone was added and thoroughly mixed. The resulting reducing lotion was then uniformly applied to the rolled sections of hair on a one half area of the scalp. The remaining portion of reducing lotion, containing no N-alkyl pyrrolidone was uniformly applied to the remaining rolled sections of hair on the other half section of the scalp. The reducing lotions were allowed to remain on the hair for a period of 8 minutes at room temperature, after which the rolled hair was thoroughly rinsed with water, allowed to drip dry and the neutralizing lotion uniformly applied to saturate the hair. The neutralizing solution was allowed to remain on the hair for 3 minutes, after which the hair was rinsed and the rods removed. The hair was again rinsed and brush dried.

The half section of the head treated with the reducing lotion containing N-dodecylpyrrolidone showed greatly improved wet and dry combability, and the hair had a silky soft texture characteristic of conditioning. The remaining half section of the hair to which the reducing lotion containing no N-dodecyl pyrrolidone was applied, showed considerably less curl and less luster. The hair in this half section was noticeably harsher to the touch and appeared dryer and more brittle, particularly at the distal ends of the hair shafts.

EXAMPLES 2-6

The general procedure outlined above in Example 1 was repeated on different subjects. In each case 1% of the N-alkyl pyrrolidone, based on total composition, was added.

The condition of the hair of test subjects is summarized in following Table I.

TABLE I

| Subject | A | B | C | D | E | F |
|---|---|---|---|---|---|---|
| Type | | | | | | |
| normal | X | X | X | X | X | X |
| tinted | | | | | | |
| bleached | | | | | | |
| Condition | | | | | | |
| good | X | X | X | X | X | X |
| fair | | | | | | |
| poor | | | | | | |
| Texture | | | | | | |
| coarse | | | | | | |
| medium | | X | | X | X | X |
| fine | X | | X | | | |
| Class | | | | | | |
| normal | X | X | X | X | X | X |
| dry | | | | | | |
| oily | | | | | | |
| Length | | | | | | |
| long | | | | | | |
| medium | | X | X | X | X | X |
| short | X | | | | | |

Following Table II reports the results of permanent waving test comparisons on the above subjects and the N-alkyl-2-pyrrolidone (NAP) employed in the one half portion of the waving lotion applied to the hair on the one side of the scalp. The other side was treated with the remaining lotion containing no N-alkyl pyrrolidone.

The tests reported in Table II used commercial cold wave hair preparations. Specifically, "Design Freedom" Cold Wave Lotion by Zotos International Inc. was used on subjects A, B, D and E. Subject C was treated with "Post Impression" Cold Wave Lotion by Helene Curtis and subject F was treated with Wella Cold Wave Lotion by Wella, Inc. All waves were carried out at full recommended processing.

TABLE II

| | SUBJECT TESTED | | | | | | | | | | | |
|---|---|---|---|---|---|---|---|---|---|---|---|---|
| | A | | B | | | C | D | | E | | F | |
| Alkyl of NAP | dodecyl | — | dodecyl | — | — | dodecyl | dodecyl | — | dodecyl | — | dodecyl | — |
| Side of scalp | right | left | right | left | right | left | right | left | right | left | right | left |
| WAVE LOTION | | | | | | | | | | | | |
| masked thio odor | good | fair | good | good | good | good | good | fair | good | good | poor | poor |
| test curl after 3 min. | good | fair | good | good | — | — | good | fair | good | fair | good | good |
| scalp sensation | none | slight | none | slight | slight | none | none | none | none | none | none | none |
| process time | 15 min. | 15 min. | 20 min. | 20 min. | 15 min. | 15 min. | 10 min. | 10 min. | 15 min. | 15 min. | 20 min. | 20 min. |
| penetration | excellent | fair | good | fair | fair | good | excellent | fair | excellent | poor | excellent | fair |
| NEUTRALIZATION | | | | | | | | | | | | |
| penetration | good | fair | excellent | fair | fair | good | excellent | fair | excellent | fair | good | fair |
| pickup | good | fair | good | good | excellent | good | good | fair | good | good | good | fair |
| thio odor | little | more | little | more | none | none | strong | stonger | strong | stronger | strong | stronger |
| scalp sensation | none | slight | none | slight | slight | none | none | none | none | none | none | none |
| HAIR EVALUATION | | | | | | | | | | | | |
| frizz | none | some | none | none | none | none | none | slight | none | slight | none | slight |
| snarling | none | slight | slight | more | slight | less | slight | more | none | some | slight | more |
| curl | good | fair | good* | good | fair | good | excellent | good | good | fair | good | fair |
| springiness | good | fair | excellent | good | fair | good | good | fair | good | fair | good | fair |
| luster | good | fair | excellent | fair | fair | good | good | fair | good | fair | good | fair |
| odor | none | none | none | strong | none | none | some | some | none | none | slight | some |
| skin irritation | none | slight | none | none | slight | none | none | none | none | none | none | none |
| feel | silky | dry | v. silky | silky | soft | silky | silky | sl. dry | silky | dry | conditnd. | sl. dry |
| REEVALUATION AFTER THREE WEEKS | | | | | | | | | | | | |
| HAIR CONDITION | | | | | | | | | | | | |
| feel | conditioned | dry | v. silky | silky | silky | silkier | silky | dry | silky | dry | conditnd. | sl. dry |
| snarling | none | slight | none | slight | fair | slight | slight | more | none | slight | slight | more |
| curl retention | high | fair | good | fair | fair | good | excellent | fair | good | fair | good | fair |
| scalp irritation | none | slight | none | none | slight | none | none | none | none | none | none | none |

*softness noted

EXAMPLES 7-15

Human hair samples of virgin dark brown, 12" length and individual tresses (3 grams, 10" length) were saturated with water, allowed to drip and subjected to treatment simulating the treatment outlined in Example 1. Specifically, each hair sample was rolled on a permanent waving rod and the reducing solution of Example 1 to which was added the following N-alkyl pyrrolidone compounds in the amount indicated below was poured over the hair sample and allowed to remain for 10 minutes at room temperature. Each hair sample was then rinsed with water, allowed to drip and the neutralizing solution of Example 1 was applied and allowed to remain on the hair for a period of 3 minutes, after which it was removed by water washing. The hair was then unrolled and allowed to dry. In each case the resulting hair samples showed a conditioning effect and had a soft, silky texture. There was no loss in curl retention after shampooing and the residence time of the reducing lotion was significantly reduced over 15 minutes normally required for effective waving. The N-alkyl pyrrolidone additives employed were as follow:

| Example | Alkyl group of the N—alkyl Pyrrolidone | % by Weight based on total reducing lotion |
|---|---|---|
| 7 | N—octadecyl | 1.00 |
| 8 | N—hexadecyl | 1.00 |
| 9 | N—octyl | 1.00 |
| 10 | N—isoctyl | 1.00 |
| 11 | N—hydrogenated tallow | 1.00 |
| 12 | N—coco | 1.00 |
| 13 | N—dodecyl | 0.05 |
| 14 | N—dodecyl | 5.00 |
| 15 | 50/50 mixture of N—dodecyl and N—hexadecyl | 1.00 |

EXAMPLE 16

An exothermic permanent waving preparation representative of standard professional heat waving preparation was prepared for this test. The preparation contained a waving lotion and a neutralizing lotion having the following compositions.

| | % by Weight |
|---|---|
| A REDUCING LOTION | |
| Ammonium thioglycolate (60 wt. %) | 27.60 |
| HAMPOL 120* | 0.28 |
| Aqueous ammonia (28%) | 3.43 |
| Ethoxylated lauryl alcohol (BRIT 35) | 0.78 |
| Deionized water | Q.S. |
| Fragrance | 0.18 |

-continued

| | % by Weight |
|---|---|
| | 100.00 |
| B HEAT ACTIVATING LOTION | |
| Hydrogen peroxide (35%) | 12.63 |
| Disodium phosphate | 0.10 |
| Phosphoric acid | 0.08 |
| Deionized water | 87.19 |
| | 100.00 | pH adjusted to 8.8 with $H_2SO_4$ or aqueous ammonia
*trisodium-N—hydroxyethyl, ethylene diamine triacetate The hair of test subject was normal, of medium texture and good condition. In the present treatment, the hair of test subject was saturated with water, allowed to drip dry, after which the hair was sectioned into about 25 sections and the distal ends of each section is wrapped in a porous end paper and rolled on a permanent hair setting rod. To 91 ml of lotion A was added 20 ml of lotion B and an 18° to 20° rise in temperature was noted. Thiglycolic acid (9.2%) of the combined lotions was then added.

To a one half portion of the above mixed lotions, 1.00% by weight of N-dodecylpyrrolidone was added and thoroughly mixed. The resulting reducing lotion was then uniformly applied to the rolled sections of hair on the left half area of the scalp. The remaining portion of mixed lotion, containing no N-alkyl pyrrolidone, was uniformly applied to the remaining rolled sections of hair on the right half section of the scalp. The reducing lotions were allowed to remain on the hair for a period of 15 minutes at ambient temperature, after which the rolled hair was thoroughly rinsed with water, allowed to drip dry and the rods removed. The hair was again rinsed and brush dried.

The half section of the head treated with the mixed lotion containing N-dodecylpyrrolidone showed greatly improved wet and dry combability, and the hair had a silky soft texture characteristic of conditioning. The remaining half section of the hair to which the mixed lotion containing no N-dodecyl pyrrolidone was applied, showed considerably less curl and less luster. The hair in this half section was noticeably harsher to the touch and appeared dryer and more brittle, particularly at the distal ends of the hair shafts. Following Table III summarizes the results of this experiment.

TABLE III

| | HAIR ON | |
|---|---|---|
| | Right Side | Left Side |
| WAVE LOTION EFFECTS | | |
| masked thio odor | fair | good |
| test curl (after 3") | good | excellent |
| hair penetration | fair | good |
| pick up | good | good |
| scalp sensation | slight | none |
| HAIR EVALUATION | | |
| frizzy | slight | none |
| snarling | slight | none |
| curl | soft | very soft |
| springiness | good | very good |
| luster | fair | very good |
| feel | dry | silky |
| odor | slight | none |
| skin irritation | none | none |

Having thus described the invention we claim.

What is claimed is:

1. A composition comprising a permanent structure altering lotion for hair containing a reducing agent suitable for relaxation of the hair fiber structure and a sufficient hair fiber protective and conditioning amount of an N-alkyl lactam having a 5 to 7 membered heterocyclic ring and from 8 to 22 carbon atoms in said alkyl group.

2. The composition of claim 1 wherein said lactam is an N-alkyl pyrrolidone.

3. The composition of claim 1 wherein said lotion is a permanent waving lotion.

4. The composition of claim 1 wherein said lotion is a permanent hair straightening lotion.

5. The composition of claim 1 wherein said reducing agent is selected from the group consisting essentially of a mono- or di-thioglycolate or an alkali or ammonium salt thereof; a sodium or potassium borate; and alkali sulfite; a bisulfite or an alkali or ammonium salt thereof optionally employed in admixture with urea; glyceryl monothioglycolate; thioglycolic acid; dithio glycolic acid; mercaptoethyl amine; mercaptopropionic acid; potassium or sodium hydroxide or carbonate optionally employed in admixture with guanidine and mixtures of said reducing agents.

6. The composition of claim 5 wherein said reducing agent is an aqueous solution of ammonium thioglycolate.

7. The composition of claim 5 wherein said reducing agent is an ammonium bisulfite/urea mixture.

8. The composition of claim 5 wherein said reducing agent is dithiodiammonium glycolate.

9. The composition of claim 5 wherein said reducing agent is sodium or potassium hydroxide.

10. The composition of claim 2 wherein said N-alkyl pyrrolidone is N-dodecyl pyrrolidone and wherein the lotion contains between about 0.75% and about 1.5% of said N-dodecyl pyrrolidone.

11. The composition of claim 1 wherein said lotion contains between about 0.01% and about 7.00% by weight of said N-alkyl lactam.

12. The composition of claim 1 wherein said lotion contains between about 0.05% and about 5.0% by weight of said N-alkyl lactam.

13. The composition of claim 2 wherein said composition contains said hair reducing agent, a neutralizing amount of a neutralizing agent for said reducing agent and N-alkyl pyrrolidone in a concentration sufficient to protect and condition the hair against damage.

14. The composition of claim 13 wherein said neutralizing agent is selected from the group consisting essentially of hydrogen peroxide; barium or calcium chloride; a sodium or potassium perborate or bromate, perbromate, or percarbonate optionally employed in admixture with guanidine and mixtures of said neutralizing agents.

15. The composition of claim 13 where the N-alkyl pyrrolidone comprises a portion of at least one of said reducing and neutralizing agents.

16. A process for permanently altering the configuration of hair without damage which includes the steps of
(a) imparting the desired configuration to the hair
(b) treating the hair with an aqueous alkaline solution containing a keratin reducing agent sufficient to relax the hair fiber structure and an N-alkyl lactam having a 5 to 7 membered heterocyclic ring and 8 to 22 carbon atoms in said alkyl group in a mole ratio of from about 3:1 to about 30:1 reducing agent to lactam at a pH of from about 7 to about 10.5 for a period sufficient to obtain a permanent hair configuration alteration without hair damage and (c) fixing the hair fiber structure in said altered configuration.

17. The process of claim 16 wherein said reducing agent is selected from the group consisting essentially of a mono- or di-thioglycolate; or an alkali or ammonium salt thereof; a sodium or potassium borate; an alkali sulfite; a bisulfite or an alkali or ammonium salt thereof optionally employed in admixture with urea; glyceryl monothioglycolate; thioglycolic acid; dithioglycolic acid; mercaptoethyl amine; mercaptopropionic acid; potassium or sodium hydroxide or carbonate optionally employed in admixture with guanidine and mixtures of said reducing agents.

18. The process of claim 16 wherein said N-alkyl lactam is an N-alkyl pyrrolidone having from 12 to 26 carbon atoms.

19. The process of claim 16 which is a permanent hair curling process.

20. The process of claim 16 which is a permanent hair straightening process.

21. The process of claim 18 wherein said fixing step is effected by adding a neutralizing amount of a neutralizing agent for said reducing agent and wherein said N-alkyl pyrrolidone is added to at least one of said reducing and said neutralizing agents in a concentration of between about 0.01% and about 7.00% by weight based on the total volume of the agent to which it is added.

22. The process of claim 21 wherein said neutralizing agent is selected from the group consisting essentially of hydrogen peroxide; barium or calcium chloride; a sodium or potassium perborate, bromate, perbromate, or percarbonate optionally employed in admixture with guanidine and mixtures of said neutralizing agents.

23. A method for permanently altering the configuration of hair without damage including the steps of
   (a) imparting the desired configuration to the hair
   (b) treating the hair with an aqueous alkaline solution containing a mercaptan keratin reducing agent and an N-alkyl-pyrrolidone having from 12 to 26 carbon atoms in a mole ratio of from about 3:1 to about 30:1 reducing agent to N-alkyl pyrrolidone at a pH of from about 7 to about 10.5 for a period sufficient to obtain a permanent hair configuration alteration without damage to the hair and
   (c) fixing said altered configuration.

24. The process of claim 23 wherein the mole ratio of reducing agent to N-alkyl pyrrolidone is between about 8:1 and about 20:1.

* * * * *